United States Patent

Rudnic et al.

[11] Patent Number: 5,912,013
[45] Date of Patent: Jun. 15, 1999

[54] ADVANCED DRUG DELIVERY SYSTEM AND METHOD OF TREATING PSYCHIATRIC, NEUROLOGICAL AND OTHER DISORDERS WITH CARBAMAZEPINE

[75] Inventors: Edward M. Rudnic, North Potomac; George W. Belendiuk, Potomac, both of Md.; John McCarty, Biscayne Park, Fla.; Sandra Wassink, Frederick; Richard A. Couch, Germantown, both of Md.

[73] Assignee: Shire Laboratories, Inc., Rockville, Md.

[21] Appl. No.: 08/426,394

[22] Filed: Apr. 21, 1995

Related U.S. Application Data

[63] Continuation of application No. PCT/US92/06123, Jul. 23, 1992, which is a continuation-in-part of application No. 07/734,541, Jul. 23, 1991, Pat. No. 5,326,570.

[51] Int. Cl.[6] .............................. A61K 47/32; A61K 9/22
[52] U.S. Cl. .......................... 424/465; 424/468; 424/482; 424/489
[58] Field of Search ................................. 424/489, 772.4, 424/465

[56] References Cited

U.S. PATENT DOCUMENTS

| | | |
|---|---|---|
| 4,606,909 | 8/1986 | Bechgaard et al. . |
| 4,794,001 | 12/1988 | Mehta et al. . |
| 4,801,460 | 1/1989 | Goertz et al. . |
| 4,857,336 | 8/1989 | Khanna et al. . |
| 4,935,245 | 6/1990 | Horn et al. ............................... 424/489 |
| 4,942,182 | 7/1990 | Weiss et al. . |
| 4,980,170 | 12/1990 | Schneider et al. . |
| 4,992,278 | 2/1991 | Khanna et al. ........................ 424/473 |
| 5,009,894 | 4/1991 | Hsiao . |
| 5,023,272 | 6/1991 | Burch et al. . |
| 5,284,662 | 2/1994 | Koparkar et al. ........................ 424/473 |
| 5,326,570 | 7/1994 | Rudnic et al. ........................... 424/458 |

OTHER PUBLICATIONS

CA. 118:175826 K. Glaenzer et al Apr. 1993.

CA 121:117693 H. Mimose et al Feb. 1994.

CA: 121:91463 Zingope et al 1994.

Primary Examiner—Peter F. Kulkosky
Attorney, Agent, or Firm—Elliot M. Olstein; Raymond J. Lillie

[57] ABSTRACT

The present invention relates to a composition and method of treating a patient by administering carbamazepine in a pharmaceutical dosage form capable of maintaining the patient's blood concentration at from about 4 μg/ml to about 12 μg/ml over at least a 12 hour period, where the blood concentration of carbamazepine does not vary by more than 60 percent.

10 Claims, 1 Drawing Sheet

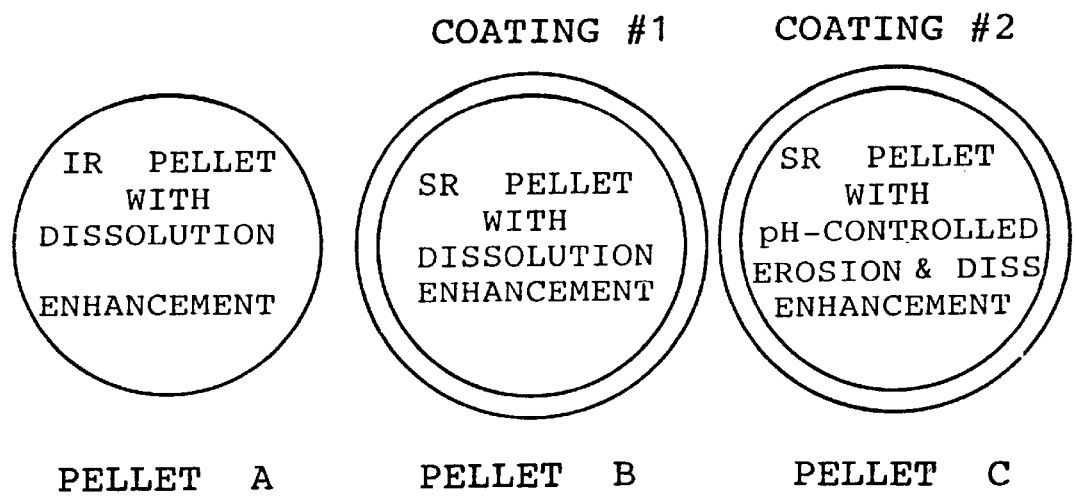
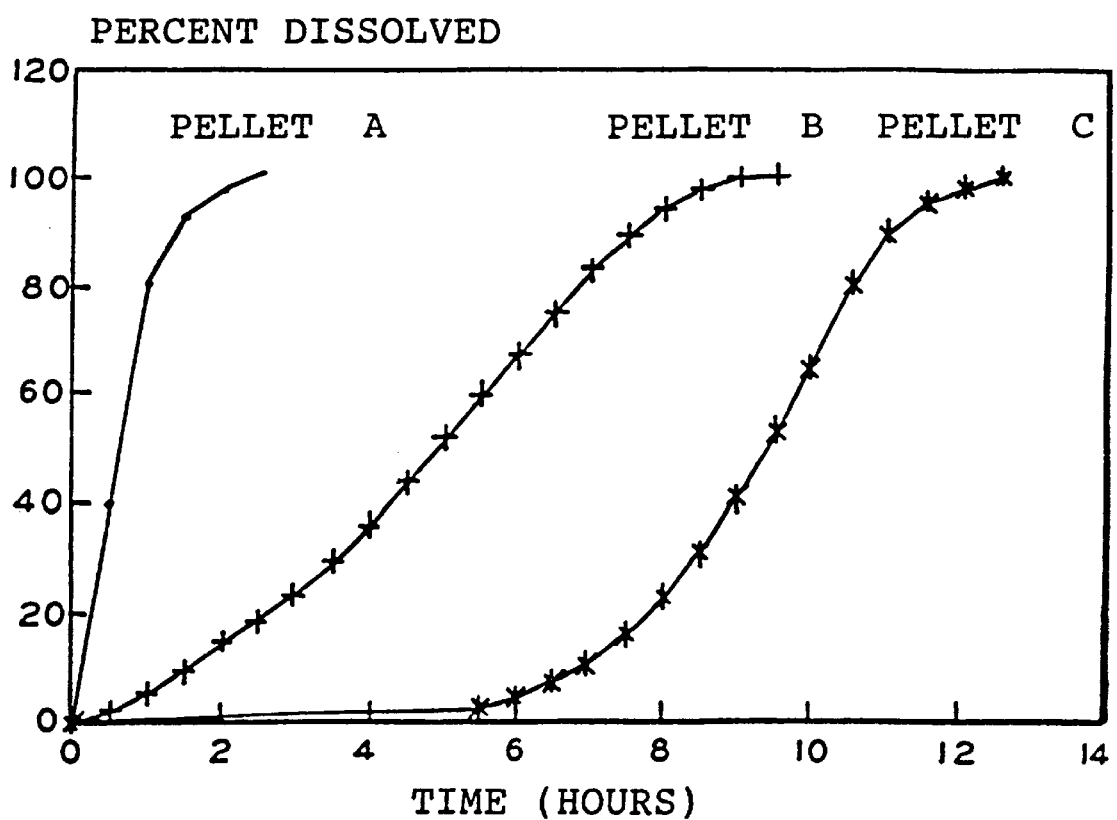

ADVANCED DRUG DELIVERY SYSTEM AND METHOD OF TREATING PSYCHIATRIC, NEUROLOGICAL AND OTHER DISORDERS WITH CARBAMAZEPINE

This application is a continuation of International Application No. PCT/US92/06123, filed Jul. 23, 1992, which is a continuation-in-part of Application Ser. No. 07/734,541, filed Jul. 23, 1991, now U.S. Pat. No. 5,326,570.

The present invention relates to a method of delivery for carbamazepine which will provide steady and consistent blood levels of carbamazepine. The blood levels of carbamazepine are within a therapeutic range required for the treatment of epilepsy as well as other psychiatric, neurological and other disorders.

Carbamazepine is an iminostilbene derivative that is used clinically to treat seizure disorders, trigeninal neuralgia, and most recently, manic depressive illness.

Carbamazepine is also known to those skilled in the art to be insoluble or difficult to solubilize. In addition, it is also difficult to achieve high loading of such a carbamazepine in a pellet form. The term high loading as used in this application shall mean at least sixty percent (60%) by weight of such carbamazepine. As used herein and as known in the art, the term robust pellets shall mean pellets capable of retaining their physical integrity during and after processing into a dosage form and undergoing standard coating procedures.

The present invention provides a method and composition for delivery of carbamazepine which provides steady and consistent blood levels of carbamazepine within a therapeutic range. The therapeutic range is from about 6 $\mu$g/ml to about 12 $\mu$g/ml of carbamazepine over a period of time. Blood levels of carbamazepine of less than 4 $\mu$g/ml have been found to be ineffective in treating clinical disorders and blood levels greater than 12 $\mu$g/ml have been found to be likely to result in undesirable side effects such as neuromuscular disturbances, cardiovascular and gastrointestinal effects.

The present invention provides for the maintenance of blood levels of carbamazepine (C) so as to minimize Cmax/Cmin variation or fluctuation. An acceptable fluctuation in the blood level Cmin/cmax ratio would be a range of from about 0.6 to about 1.0. Most preferably, the variation or fluctuation would range from about 0.8 to about 1.0.

The present invention maintains a therapeutic range of blood levels of carbamazepine effective for the treatment of disorders which include but are not limited to depression, trigeminal; neuralgia; chronic pain states; headaches; addictive states for: cocaine, alcohol, opiates and nicotine; other obsessive compulsive disorders and cardiovascular disease.

An embodiment of the present invention provides for a sustained release method of delivery of carbamazepine which is to be administered at least once a day, preferably twice a day; therefore, in accordance with an aspect of the present invention there is provided a method for maintaining in a patient, steady and consistent blood level of carbamazepine within therapeutic range of from about 4 $\mu$g/ml to about 12 $\mu$g/ml, over a time period of at least 12 hours. In accordance with the present invention, within the hereinabove noted therapeutic range, the blood concentration of carbamazepine varies by not more than 60 percent and preferably by not more than 40 percent and most preferably by not more than 20% over a period of at least twelve hours.

The method of delivery of carbamazepine of the present invention provides for the following routes of administration sublingual, transmucosal, transdermal, parenteral and preferably oral. Parenteral administration would require an amount of carbamazepine of from about 100 mg to about 1000 mg per 12 hours. The dosage forms may include but are not limited to liquids, tablets, capsules, sprinkle dosage forms, chewable tablets, pellets and transdermal patches.

It is anticipated by this application that it may be possible to produce the pellets as described herein other than as robust pellets.

One aspect of the present invention provides for a sustained release method of delivery which includes administering one or more single unit dosage forms of equal or varying concentration of carbomazepine. Each such unit is designed to release its contents at varying times over at least a twelve hour time period so as to maintain a carbamazepine blood level within the therapeutic range previously described.

The term W/W as used herein is representative of a weight to weight ratio of the material specified to the weight of the unit dosage form as a whole.

To achieve and maintain the therapeutic range, a dose of from about 400 to about 600 mg per 12 hour period of carbamazepine is needed. Due to this, it is preferred to have greater than 30% (W/W) of the pellet content as carbamazepine. The following are representative examples of the various ingredients which may be included in the sustained-release formulation.

For carbamazepine, it is preferred to have three different types of units in a single form multiple-unit dosage form. The first unit is an immediate release dosage form, preferably in pellet form. This component can also be a powder if necessary. In either case, the pellet should have a surface-active agent such as sodium lauryl sulfate, sodium monoglycerate, sorbitan monooleate, polyoxyethylene sorbitan monooleate, glyceryl monostearate, glyceryl monooleate, glyceryl monobutyrate, any one of the Pluronic line of surface-active polymers, or any other suitable material with surface active properties or any combination of the above. Preferably the surface-active agent would be a combination of sodium monoglycerate and sodium lauryl sulfate. The concentration of these materials in this component can range from about 0.05 to about 10.0% (W//W).

The pellet should be made via a suitable process which makes the dosage form into a reasonably round unit. This process can be, for example, simple granulation, followed by seiving; extrusion and marumerization; rotogranulation; or any agglomeration process which results in a pellet of reasonable size and robustness. As stated earlier, it is also possible to have this immediate release component as a powder, although the preferred form is a pellet due to mixing and de-mixing considerations.

The materials to be admixed along with the drug and surfactant for this first pellet should possess sufficient binding properties to allow agglomeration to occur. These materials can be, but are not limited to, microcrystalline cellulose (such as Avicel), corn starch, pregelatinized starch (such as Starch 1500 or National 1551), potato starch, sodium carboxymethylated starch, sodium carboxymethylated cellulose, hydroxypropylmethyl cellulose, hydroxypropylcellulose, hydroxyethylcellulose, ethylcellulose, as well as any cellulose ether. In addition, any binder material such as gums (ex. Guar Gum) natural binders and derivatives such as alginates, chitosan, gelatin and gelatin derivatives, are also useful. Synthetic polymers such as polyvinylpyrrolidone (PVP), acrylic acid derivatives (Eudragit, Carbopol, etc.) and polyethylene glycol (PEG) are also useful as binders and matrix formers for the purpose of this invention. It may be useful to have these materials present in the range of from about 1.0 to about 60.0% (W/W)

either in total, or individually in combination with one another. Preferably, these materials should be present in the range of from about 30 to about 50 percent (W/W).

It may also be necessary to incorporate a disintegrant into these pellets in order to facilitate dissolution of the active ingredient. For this purpose, any suitable tablet disintegrant can be utilized here, such as cross-linked sodium carboxymethylcellulose (Ac-Di-Sol), cross-linked sodium carboxymethyl starch (Explotab, Primojel), cross-linked PVP (Plasdone XL) or any other material possessing tablet disintegrant properties.

For working examples of the first pellet see Examples 1 through 10 below.

The second pellet should have a sustained release profile, and needs to be able to address the changing pH of the GI tract, and its effect on the absorption of carbamazepine. This pellet should have all of the ingredients as mentioned for pellet A, as well as some organic acid which will be useful to reduce the pH of the microenvironment of the pellet, and thus facilitate dissolution. These materials are, but not limited to, citric acid, lactic acid, tartaric acid, or other suitable organic acids. These materials should be present in concentrations of from about 0 to about 15.0% (W/W), preferably these materials would be present in concentrations of from about 5.0 to about 10.0 percent (W/W). The process for manufacturing these pellets is consistent to the process described above for the previous pellet.

In addition to the pellet, this component should have a controlling coat applied to the surface of the pellet such that the release of the drug from the pellet is controlled and released over a 6–10 hour period. The materials used for this purpose can be, but are not limited to, ethylcellulose, hydroxypropylmethylcellulose, hydroxypropylcellulose, hydroxyethylcellulose, methylcellulose, nitrocellulose, carboxymethylcellulose, and any other cellulose ether, as well as copolymers of ethacrylic acid and methacrylic acid (Eudragit), or any other acrylic acid derivative (Carbopol, etc.) can be used. In addition, an enteric coating material can also be employed, either singularly, or in combination to the above non-pH sensitive coatings. These materials include, but are not limited to, hydroxypropylmethylcellulose phthalate and the phthalate esters of all the cellulose ethers. In addition, phthalate esters of the acrylic acid derivatives (Eudragit), or cellulose acetate phthalate. These coating materials can be employed in coating the surfaces in a range of from about 1.0% (W/W) to about 25% (W/W). Preferably these coating materials should be in a range of from about 8.0 to about 12.0 percent (W/W).

For working examples of the second pellet, see Examples 11 through 20 below.

The third pellet in this system should be qualitatively similar to the second pellet, in that the manufacturing process for producing this pellet is consistent with that of the first two pellets, and the microenvironment inside the pellet should be consistent with that of pellet B. However, this pellet should have some internal component breaking down in the pH of the lower GI tract. Thus, it will be necessary to include some enteric or pH sensitive material into the pellet to facilitate erosion and breakdown in the lower GI tract. This material can be, but is not limited to, cellulose acetate phthalate, hydroxypropylmethylcellulose phthalate, any additional cellulose ether phthalates, any of the acrylic acid derivative phthalates (Eudragit), as well as any enteric coating material, such as shellac, zein, or others. The concentration of these materials in the pellet should be from about 1.0 to about 15.0% (W/W), preferably the concentration of materials should be from about 5.0 to about 10.0 percent (W/W).

The coating of this third pellet should be similar to the coating for pellet B, except that it should have a considerable pH sensitivity associated with it. Therefore, it would be desirable to coat pellet C with any of the pH sensitive, or enteric coating materials listed above, either singularly, or in combination with any coating material mentioned above. This coating level of this pellet should range from about 1.0 to about 15.0% (W/W), preferably the concentration of materials should be from about 5.0 to about 12.0 percent (W/W).

For working examples of the third pellet, see Examples 21 through 28 below.

Each pellet should have its own dissolution profile associated with the formulation assigned to it.

BRIEF DESCRIPTION OF THE DRAWINGS

The target dissolution curves for the three units can be seen in FIG. 1. This figure shows a schematic of the three units, as well as the target dissolution for the materials. Depending on the formulation chosen in this invention, the exact ratios of each of the pellets may need to be adjusted. The amount of the first unit in the formulation should preferably range from about 5.0 to about 25.0%. The amount of the second unit in the dosage form should range from about 15.0 to about 90.0%. The dosage form for the third unit should be in a range of from about 5.0 to about 30.0%.

In accordance with another aspect of the present invention, there is provided a pharmaceutical composition in the form of robust pellets, in which carbamazepine is present in high loading. More particularly, the robust pellets contain the carbamazepine in an amount of at least sixty (60) percent, preferably seventy (70) percent or more, and most preferably eighty (80) percent or more by weight. The pellets are formed with a binder which is a pharmaceutically acceptable carrier which is comprised of an amphiphilic polymer having both hydrophobic and hydrophilic properties. The amphiphilic polymer preferably is also capable of forming both water in oil and oil in water emulsions; such a polymer would usually have both a hydrophobic and a hydrophilic portion. In general, such a polymer can be produced from a monomer having both a hydrophobic moiety and a hydrophilic moiety or by copolymerizing a hydrophobic monomer with a hydrophilic monomer.

In preparing the robust pellets, the amphiphilic polymer which is used as a binder or carrier in forming the robust pellets, is provided in the formulation prior to robust pellet formation. The formulation which includes the active, pharmaceutical, the hereinabove described amphiphilic polymer and any other ingredients to be included in formulating the robust pellets, is then granulated to produce solid robust pellets containing a high loading of carbamazepine. The pharmaceutically acceptable amphiphilic polymer used in the present invention may be comprised of solid amphiphilic polymer or a solution of amphiphilic polymer or a mixture of both depending upon the surface active properties of the amphiphilic polymer being used.

Although applicant does not intend to be bound to any theoretical reasoning, carbamazepine tends to be hydrophobic in nature and it is believed that amphiphilic polymers which have more hydrophobic tendencies (higher surface active properties) act as better binders for the high loading of carbamazepine. Therefore depending upon the specific amphiphilic polymer being used, and whether the polymer exhibits higher surface active properties as a solid or as a solution, will determine whether it is be best to use a mixture of a solution of the amphiphilic polymer and solid amphiphilic polymer in the robust pellet forming formulation; or whether it is best to use a solution of the amphiphilic polymer alone in the robust pellet forming formulation. The appropriate amphiphilic polymer formulation can then be granulated into robust pellets while still achieving a high loading of active insoluble pharmaceutical.

In some cases, it may also be possible to provide an amphiphilic polymer for use in the formulation by blending a polymer which does not include both a hydrophobic and a hydrophilic portion with a surfactant to thereby provide a polymer with surface activity.

When using a mixture of solid amphiphilic polymer and a solution of amphiphilic polymer in producing robust pellets, the present invention provides that the solution of the amphiphilic polymer make up no less than five percent (5%) by weight of the mixture of the solution of the amphiphilic polymer and the solid amphiphilic polymer. Preferably, the solution of the amphiphilic polymer is no more than seventy percent (70%) by weight of the total mixture of the solution of the amphiphilic polymer and the solid amphiphilic polymer. Most preferably, the solution of the amphiphilic polymer makes up from about forty percent (40%) by weight to about sixty (60%) by weight of the total mixture of the solution of the amphiphilic polymer and the solid amphiphilic polymer. In general, the polymer solution contains from 4% to 20%, by weight, of the polymer.

In another embodiment of the present invention, there is used a mixture of the amphiphilic polymer wherein the same amphiphilic polymer is to be used for both the solution and solid amphiphilic polymers. Additionally, the present invention also provides for two different amphiphilic polymers to be used for the solution and solid amphiphilic polymers.

The amphiphilic polymer used in the present invention may be any of a wide variety of pharmaceutically acceptable amphiphilic polymers. As representative examples thereof, there may be generally mentioned, all vinylpyrrolidone derivates, all polyhydroxls and all ethoxylated polymers that have surface-active properties. As representative of more specific examples there may be mentioned polyvinylpyrrolidone (PVP), PVP-VA copolymers (Kollidon VAG4), Polyether maleic anhydride, polyethylene glycol, polysorbates esterified celluloses, polyacrylates, polyvinylacetates or pluronics, for example, block copolymers of oxyethylene and oxypropylene.

In general most of pharmaceutically acceptable amphiphilic polymers, described above, should have a number average molecular weight of at least 5000 and preferably at least 50,000. In a preferred embodiment the amphiphilic polymer is polyvinylpyrrolidone, having a high number average molecular weight. High molecular weight polyvinylpyrrolidones are known in the art as having a molecular weight of at least 100,000. As representative of a polyvinylpyrrolidones having a high number average molecular weight there may be mentioned PVP K-90 which has a number average molecular weight of 360,000.

In addition to the amphiphilic polymer and carbamazepine, the pellets may include other materials used in the formation of pharmaceutical pellets. Representative examples of such ingredients may include but are not limited to pharmaceutically acceptable fillers, surface active agents, binders and disintegrants, specific examples of which are described below.

A preferred embodiment of the present invention provides that such robust pellets contain an amount of carbamazepine capable of maintaining the patient's blood concentration at from about 4 µg/ml to about 12 µg/ml over at least a 12 hour time period, where the blood concentration of carbamazepine does not vary by more than 20%.

Another embodiment of the present invention provides for a composition for treating a patient comprising an effective amount of carbamazepine and a pharmaceutically acceptable carrier which are sufficient for maintaining a blood concentration of carbamazepine within the therapeutic range and as described above.

Using such dosage form it is preferred that the dose of carbamazepine administered each 24 hour period is from about 800 mg to about 1200 mg. The dose is adjusted by the administering physician based upon the age, sex and weight of the patient to maintain therapeutic blood levels of carbamazepine.

Since carbamazepine is needed to be absorbed into the bloodstream over at least a twelve-hour period, it is preferred that the drug be administered in a dosage form that will reliably remain in the GI tract, in a sufficiently high region as to favor absorption. To achieve and maintain the therapeutic range, a dose of from about 400 to about 600 mg per 12 hour period of carbamazepine this makes it necessary to have a high loading of drug in the pellets.

Another object of the present invention provides a method for producing robust pellets of carbamazepine which comprises blending a pellet forming formulation which includes a mixture of pharmaceutically acceptable amphiphilic polymer, and an carbamazepine, which is then granulated into robust pellets.

In a preferred embodiment of the present invention the pharmaceutical composition contains at least sixty percent (60%), preferably, seventy percent (70%) or more by weight of the carbamazepine. Most preferably, the present invention provides for a pharmaceutical composition which contains eighty percent (80%) or more of the carbamazepine by weight. As representative examples of such carbamazepine there may be mentioned the following: carbamazepine, ibuprofen, gemfibrizole, flutamide, estradiol, alprazolam, triazolam, lorazepam, and indomethacin.

The term W/W as used herein is representative of a weight to weight ratio of the material specified to the weight of the unit dosage form as a whole.

In accordance with a preferred embodiment of the present invention, there is provided robust pellets in which carbamazepine is present in high loading. In a particularly preferred embodiment there is produced three different types of pellets containing carbamazepine as the carbamazepine, one of which is an immediate release formulation, the second of which is a slow release formulation and the third of which is an pH-dependent formulation.

In general, the three different types of pellets are combined into a single dosage form for oral delivery. The immediate release formulation has a high loading of carbamazepine and may or may not be formed as a robust pellet formulation. However, the pellet is formed it must allow for the quick release of the carbamazepine. The slow release and pH-dependent formulation are formulated as robust pellets with a high loading of carbamazepine, most preferably, by using a high number average molecular weight polyvinylpyrrodidone having a number average molecular weight of at least 100,000, as the amphiphilic polymer (the carrier or binder) for forming the robust pellets. In producing the robust pellets the polyvinylpyrrolidone (PVP) is preferably provided in the formulation, prior to pellet formation, as a solution of PVP. Although having 100% of the amphiphilic polymer in solution is preferred, it may be possible to utilize a mixture of both solid polyvinylpyrrolidone (PVP) and a solution of polyvinylpyrrolidone, wherein the solution of PVP is no less than fifty percent (50%) of the mixture, preferably no less than seventy percent (70%) of the mixture of solid PVP and solution of PVP. The PVP solution should contain from about 4% to about 20% by weight of the PVP.

In addition to the high loading of carbamazepine, the first unit is formulated with ingredients of a type generally employed in producing an immediate release dosage form. These materials can be, but are not limited to, microcrystalline cellulose (such as Avicel), corn starch, pregelatinized starch (such as Starch 1500 or National 1551), potato, starch, sodium carboxymethylated starch, sodium carboxymethylated cellulose, hydroxypropylmethyl cellulose, hydroxypropylcellulose, hydroxyethylcellulose, ethylcellulose, as well as any cellulose ether.

It may also be necessary to incorporate a disintegrant into this first unit in order to facilitate dissolution of the carbamazepine. For this purpose, any suitable tablet disintegrant can be utilized here, such as cross-linked sodium carboxymethylcellulose (Ac-Di-Sol), cross-linked sodium carboxymethyl starch (Explotab, Primojel), cross-linked PVP (Plasdone XL) or any other material possessing tablet disintegrant properties.

In the second unit, in addition to the carbamazepine and PVP the unit is formulated with ingredients of a type generally employed in producing a sustained release dosage form. These ingredients need to be able to address the changing pH of the GI tract, and its effect on the absorption of carbamazepine. This pellet should have some organic acid which will be useful to reduce the pH of the microenvironment of the pellet, and thus facilitate dissolution. These materials are, but not limited to, citric acid, lactic acid, tartaric acid, or other suitable organic acids. These materials should be present in concentrations of from about 1 to about 15.0% (W/W), preferably these materials would be present in concentrations of from about 5.0 to about 10.0 percent (W/W). The process for manufacturing these units are consistent with the process-described above for the first unit.

In addition the second unit should have a controlling coat applied to the surface of the unit such that the release of the pharmaceutical from the unit is controlled and released over a 6–10 hour period. The materials used for this purpose can be, but are not limited to, ethylcellulose, hydroxypropylmethylcellulose, hydroxypropylcellulose, hydroxyethylcellulose, methylcellulose, nitrocellulose, carboxymethylcellulose, and any other cellulose ether, as well as copolymers of ethacrylic acid and methacrylic acid (Eudragit), or any other acrylic acid derivative (Carbopol, etc.) can be used. In addition, an enteric coating material can also be employed, either singularly, or in combination to the above non-pH sensitive coatings. These materials include, but are not limited to, hydroxypropylmethylcellulose phthalate and the phthalate esters of all the cellulose ethers. In addition, phthalate esters of the acrylic acid derivatives (Eudragit), or cellulose acetate phthalate. These coating materials can be employed in coating the surfaces in a range of from about 1.0% (W/W) to about 25% (W/W). Preferably these coating materials should be in a range of from about 10.0 to about 20.0 percent (W/W).

In addition to the carbamazepine and PVP the third unit is formulated with ingredients of a type generally employed in producing ph dependent release dosage form. These ingredients should be qualitatively similar to the second unit, in that both the manufacturing process, and the microenvironment inside the unit should be consistent with that of the second unit. However, this unit should have some internal component for breaking down in the pH of the lower GI tract. Thus, it will be necessary to include some enteric or pH sensitive material into the unit to facilitate erosion and breakdown in the lower GI tract. This material can be, but is not limited to, cellulose acetate phthalate, hydroxypropylmethylcellulose phthalate, any additional cellulose ether phthalates, any of the acrylic acid derivative phthalates (Eudragit), as well as any enteric coating material, such as shellac, zein, or others. The concentration of these materials in the unit should be from about 0 to about 15.0% (W/W), preferably the concentration of materials should be from about 0 to about 5 percent (W/W).

The coating of this third unit should be similar to the coating for the second unit, except that it should have a considerable pH sensitivity associated with it. Therefore, it would be desirable to coat the third unit with any of the pH sensitive, or enteric coating materials listed above, either singularly, or in combination with any coating material mentioned above. The coating level of this unit should range from about 1.0 to about 25.0% (W/W), preferably the concentration of materials should be from about 10.0 to about 20.0 percent (W/W).

For working examples of robust core pellet formulations, see Examples 29 through 34 below.

Each pellet should have its own dissolution profile associated with the formulation assigned to it. The target dissolution curves for the three units can be seen in FIG. 1. This figure shows a schematic of the three units, as well as the target dissolution for the materials. Depending on the formulation chosen in this invention, the exact ratios of each of the pellets may need to be adjusted. The amount of the first unit in the formulation should preferably range from about 5.0 to about 25.0%. The amount of the second unit in the dosage form should range from about 15.0 to about 70.0%. The dosage form for the third unit should be in a range of from about 5.0 to about 30.0%.

The formulation described above may for example be used in the treatment of epilepsy as well as other psychiatric, neurological and other disorders. With respect to such treatment, the amount of carbamazepine administered within the 3-unit formulation should be from about 800 mg to about 1200 mg over a 24 hour period. Preferably, carbamazepine is administered within the formulation is in an amount equal to from about 400 mg to 600 mg over a 24 hour period. The therapeutic blood dosage level of the patient being treated should not be less than 4 $\mu$g/ml and should not exceed 12 $\mu$g/ml of carbamazepine over at least a 12 hour time period. The dose would be adjusted by the administering physician based upon the age, sex and weight of the patient to maintain therapeutic blood dosage levels.

The following examples 1 through 29 are intended to further illustrate not to limit the present invention. The examples are representative of formulations for carbamazepine which do not require robust pellets but which are provided three groups, one for each pellet type as described above.

| Pellet A: Immediate Release Component | | |
|---|---|---|
| | Percent | Kilograms |
| Example 1: | | |
| Microcrystalline Cellulose, N.F. (MCC) (Avicel PH-101/102, Emcocel, etc.) | 40.0 | 0.4 |
| Hydroxypropylmethylcellulose (HPMC) (Methocel E5/E50/K5/K50) | 2.5 | 0.025 |
| Croscarmellose, Type A, N.F. (Ac-Di-Sol) | 2.0 | 0.02 |
| Sodium Lauryl Sulfate (SLS) | 0.1 | 0.001 |
| Carbamazepine | 55.4 | 0.554 |
| Total | 100.0 | 1.000 |

| Pellet A: Immediate Release Component | Percent | Kilograms |
|---|---|---|
| Example 2: | | |
| MCC | 40.0 | 0.4 |
| HPMC | 5.0 | 0.05 |
| Sodium Starch Glycolate, N.F. (Explotab, Primojel) | 8.0 | 0.08 |
| SLS | 0.3 | 0.003 |
| Carbamazepine | 46.7 | 0.467 |
| Total | 100.0 | 1.000 |
| Example 3: | | |
| MCC | 20.0 | 0.2 |
| Pre-gelatinized Starch (STARCH 1500, National 1551) | 15.0 | 0.15 |
| Croscarmellose | 5.0 | 0.05 |
| Corn Starch, U.S.P. (as paste) | 5.0 | 0.05 |
| Dioctyl Sodium Sulfosuccinate (DDS) | 0.5 | 0.005 |
| Carbamazepine | 54.5 | 0.545 |
| Total | 100.0 | 1.000 |
| Example 4: | | |
| MCC | 15.0 | 0.15 |
| MCC/Carboxymethyl Cellulose (CMC) (Avicel RC Grade) | 15.0 | 0.15 |
| Croscarmellose | 5.0 | 0.05 |
| SLS | 0.5 | 0.005 |
| Carbamazepine | 64.5 | 0.645 |
| Total | 100.0 | 1.000 |
| Example 5: | | |
| MCC/CMC | 20.0 | 0.2 |
| Croscarmellose | 3.0 | 0.03 |
| Sodium Starch Glycolate | 5.0 | 0.05 |
| HPMC | 8.0 | 0.08 |
| DDS | 0.5 | 0.005 |
| Carbamazepine | 63.5 | 0.635 |
| Total | 100.0 | 1.000 |
| Example 6: | | |
| MCC | 10.0 | 0.10 |
| MCC/CMC | 10.0 | 0.10 |
| Croscarmellose | 5.0 | 0.05 |
| DDS | 0.5 | 0.005 |
| Carbamazepine | 74.5 | 0.745 |
| Total | 100.0 | 1.000 |
| Example 7: | | |
| MCC/CMC | 25.0 | 0.25 |
| Polyacrylic Acid (Carbomer) | 10.0 | 0.1 |
| SLS | 0.2 | 0.002 |
| Sodium Starch Glycolate | 7.5 | 0.075 |
| Carbamazepine | 57.3 | 0.573 |
| Total | 100.0 | 1.000 |
| Example 8: | | |
| MCC | 30.0 | 0.30 |
| HPMC | 7.5 | 0.075 |
| Croscarmellose | 5.0 | 0.05 |
| Sodium bis-(2-ethylhexyl)sulfosuccinate (Aerosol OT) | 1.5 | 0.015 |
| Carbamazepine | 56.0 | 0.560 |
| Total | 100.0 | 1.000 |
| Example 9: | | |
| MCC | 25.0 | 0.25 |
| HPMC | 5.0 | 0.05 |
| Mono/Di/Tri-glyceride Mixture (Atmul-84S) | 10.0 | 0.1 |
| SLS | 0.5 | 0.005 |
| Carbamazepine | 59.5 | 0.595 |
| Total | 100.0 | 1.000 |
| Example 10: | | |
| MCC | 25.0 | 0.25 |
| Polyvinylpyrrolidone (PVP) (Plasdone) | 8.0 | 0.08 |
| Sodium Monoglycerate (Myvaplex) | 8.0 | 0.08 |
| SLS | 0.35 | 0.0035 |
| Carbamazepine | 58.65 | 0.5865 |
| Total | 100.00 | 1.0000 |
| Example 11: | | |
| MCC | 30.0 | 0.3 |
| HPMC | 5.0 | 0.05 |
| Sodium Monoglycerate | 8.0 | 0.08 |
| Tartaric Acid | 5.0 | 0.05 |
| SLS | 0.2 | 0.002 |
| Carbamazepine | 51.8 | 0.518 |
| Total | 100.0 | 1.000 |
| Coating: | | |
| Ethacrylic/Methacrylic Acid Esters (Eudragit RS100) | 45.0 | 0.45 |
| Ethacrylic/Methacrylic Acid Esters (Eudragit RL100) | 45.0 | 0.45 |
| Propylene Glycol | 9.0 | 0.09 |
| Talc | 1.0 | 0.01 |
| Total | 100.0 | 1.00 |
| Example 12: | | |
| Same core pellet as in example 11 | | |
| Coating: | | |
| HPMC (Methocel E50) | 45.0 | 0.45 |
| Ethylcellulose (Ethocel) | 45.0 | 0.45 |
| Polyethylene Glycol 400 (PEG400) | 10.0 | 0.10 |
| Total | 100.0 | 1.00 |
| Example 13: | | |
| Same core pellet as in example 11 | | |
| Coating: | | |
| HPMC | 20.0 | 0.20 |
| Ethylcellulose | 70.0 | 0.70 |
| PEG400 | 10.0 | 0.10 |
| Total | 100.0 | 1.00 |
| Example 14: | | |
| MCC | 15.0 | 0.15 |
| MCC/CMC Mixture | 15.0 | 0.15 |
| Citric Acid | 6.0 | 0.06 |
| DSS | 0.8 | 0.008 |
| Carbamazepine | 63.2 | 0.632 |
| Total | 100.0 | 1.000 |
| Coating: | | |
| HPMC (Methocel K5M) | 10.0 | 0.10 |
| HPMC (Methocel E50) | 14.0 | 0.14 |
| Ethylcellulose | 66.0 | 0.66 |
| PEG400 | 10.0 | 0.10 |
| Total | 100.0 | 1.00 |
| Example 15: | | |
| Core pellet from example 14 | | |
| Coating from example 11 | | |

Pellet A: Immediate Release Component

|  | Percent | Kilograms |
|---|---|---|
| Example 16: | | |
| Core pellet from example 14 | | |
| Coating from example 12 | | |
| Example 17: | | |
| Core pellet from example 14 | | |
| Coating from example 13 | | |
| Example 18: | | |
| MCC | 30.0 | 0.3 |
| PVP | 8.0 | 0.08 |
| Mono/Di/Tri-Glyceride Mixture | 8.0 | 0.08 |
| SLS | 0.3 | 0.003 |
| Tartaric Acid | 7.5 | 0.075 |
| Carbamazepine | 46.2 | 0.462 |
| Total | 100.0 | 1.000 |
| Coating: | | |
| Coating from example 11 | | |
| Example 19: | | |
| Core pellet from example 18 | | |
| Coating from example 12 | | |
| Example 20: | | |
| Core pellet from example 18 | | |
| Coating from example 13 | | |
| Example 21: | | |
| Core pellet from example 18 | | |
| Coating from example 14 | | |

Pellet C: Delayed Release Component

|  | Percent | Kilograms |
|---|---|---|
| Example 22: | | |
| Core Pellet: | | |
| MCC | 25.0 | 0.25 |
| Hydroxypropylmethylcellulose Phthalate (HPMCP) | 10.0 | 0.10 |
| Tartaric Acid | 10.0 | 0.10 |
| Sodium Monoglycerate | 7.5 | 0.075 |
| DSS | 0.5 | 0.005 |
| Carbamazepine | 47.0 | 0.470 |
| Total | 100.0 | 1.000 |
| Coating: | | |
| Cellulose Acetate Phthalate (CAP) | 60.0 | 0.60 |
| Ethylcellulose | 25.0 | 0.25 |
| PEG400 | 15.0 | 0.15 |
| Total | 100.0 | 1.00 |
| Example 23: | | |
| Core pellet from example 22 | | |
| Coating: | | |
| Ethacrylic/Methacrylic Acid Esters (Eudragit line of enteric polymers) | 85.0 | 0.85 |
| Propylene Glycol | 14.0 | 0.14 |
| Talc | 1.0 | 0.01 |
| Total | 100.0 | 1.00 |

Pellet C: Delayed Release Component

|  | Percent | Kilograms |
|---|---|---|
| Example 24: | | |
| Core pellet from example 22 | | |
| Coating: | | |
| CAP | 65.0 | 0.65 |
| HPMCP | 15.0 | 0.15 |
| PEG 400 | 10.0 | 0.10 |
| PEG 8000 | 10.0 | 0.10 |
| Total | 100.0 | 1.00 |
| Example 25: | | |
| Core Pellet: | | |
| MCC | 25.0 | 0.25 |
| Mono/Di/Tri-glyceride Mixture | 15.0 | 0.15 |
| Tartaric Acid | 10.0 | 0.10 |
| CAP | 10.0 | 0.10 |
| DSS | 0.8 | 0.008 |
| Carbamazepine | 39.2 | 0.392 |
| Total | 100.0 | 1.000 |
| Coating as in example 22 | | |
| Example 26: | | |
| Core pellet as in example 25 | | |
| Coating as in example 23 | | |
| Example 27: | | |
| Core Pellet as in example 25 | | |
| Coating as in example 24 | | |
| Example 28: | | |
| Core pellet as in example 25 | | |
| Coating: | | |
| Shellac | 85.0 | 0.85 |
| Mineral Oil | 13.0 | 0.13 |
| SLS | 0.5 | 0.005 |
| Talc | 1.5 | 0.015 |
| Total | 100.0 | 1.000 |
| Example 29: | | |
| Core pellet as in example 22 | | |
| Coating as in example 28 | | |

The following Examples 30–35 represent robust core pellet formulations. The pellet should be made via a suitable process which makes the dosage form into a reasonably round unit. This process can be, for example, simple granulation, followed by sieving, extrusion and marumerization; rotogranulation; or any agglomeration process which results in a pellet of reasonable size and robustness. To produce enteric or pH dependent or sustained release robust pellets one would need to coat these robust core pellets with the appropriate coating.

EXAMPLE 30

| % W/W | INGREDIENT | AMOUNT |
|---|---|---|
| 80.00 | Carbamazepine, USP | 32.00 kg |
| 2.5 | Microcrystalline Cellulose, NF (Avicel PH-101) | 1.00 kg |
| 5.0 | Lactose, NF (Hydrous, 310) | 2.00 kg |
| 5.0 | Tataric Acid, USP (Anhydrous) | 2.00 kg |
| 0.5 | Sodium Lauryl Sulfate, NF | 0.20 kg |
| 5.0 | PVP-VA Copolymer (Kolidon VAG4) | 2.00 kg |
| 1.5 | Talc, USP | 0.60 kg |

EXAMPLE 30

| % W/W | INGREDIENT | AMOUNT |
|---|---|---|
| 0.5 | Polyethylene Glycol 400, NF | 0.20 kg |
| * | Purified Water, USP | 12.00 kg |
| 100.00 | | 40.00 kg |

*Purified Water, USP is removed during processing.

EXAMPLE 31

| % W/W | INGREDIENT | AMOUNT |
|---|---|---|
| 80.00 | Carbamazepine, USP | 32.00 kg |
| 2.5 | Microcrystalline Cellulose, NF (Avicel PH-101) | 1.00 g |
| 5.0 | Lactose, NF (Hydrous, 310) | 2.00 kg |
| 5.0 | Citric Acid, USP (Anhydrous) | 2.00 kg |
| 0.5 | Sodium Lauryl Sulfate, NF | 0.20 kg |
| 5.0 | Povidone, USP (K-90) | 2.00 kg |
| 1.5 | Talc, USP | 0.60 kg |
| 0.5 | Polyethylene Glycol 400, NF | 0.20 kg |
| * | Purified Water, USP | 12.00 kg |
| 100.00 | | 40.00 kg |

*Purified Water, USP is removed during processing.

EXAMPLE 32

| % W/W | INGREDIENT | AMOUNT |
|---|---|---|
| 80.00 | Carbamazepine, USP | 32.00 kg |
| 5.0 | Microcrystalline Cellulose, NF (Avicel PH-101) | 2.00 kg |
| 2.5 | Lactose, NF (Hydrous, 310) | 1.00 kg |
| 5.0 | Ascorbic Acid, USP (Anhydrous) | 2.00 kg |
| 0.5 | Sodium Lauryl Sulfate, NF | 0.20 kg |
| 4.0 | Polyethylene Glycol 8000 | 1.60 kg |
| 1.0 | Polyethylene Glycol 400 | 0.40 kg |
| 1.5 | Talc, USP | 0.60 kg |
| * | Purified Water, USP | 12.00 kg |
| 100.00 | | 40.00 kg |

*Purified Water, USP is removed during processing.

EXAMPLE 33

| % W/W | INGREDIENT | AMOUNT |
|---|---|---|
| 80.00 | Carbamazepine, USP (Screened) | 32.00 kg |
| 2.5 | Microcrystalline Cellulose, NF (Avicel PH-101) | 1.00 kg |
| 5.0 | Lactose, NF (Hydrous, 310) | 2.00 kg |
| 5.0 | Tartaric Acid, USP (Anhydrous) | 2.00 kg |
| 0.5 | Sodium Lauryl Sulfate, NF | 0.20 kg |
| 5.0 | Polyether Maleic Anhydride | 2.00 kg |
| 0.5 | Magnesium Stearate, USP | 0.20 kg |
| 1.0 | Talc, USP | 0.40 kg |
| 0.5 | Poloxainer 338 | 0.220 kg |
| * | Purified Water, USP | 12.00 kg |
| 100.00 | | 40.00 kg |

*Purified Water, USP is removed during processing.

EXAMPLE 34

| % W/W | INGREDIENT | AMOUNT |
|---|---|---|
| 80.00 | Carbamazepine, USP | 32.00 kg |
| 2.5 | Microcrystalline Cellulose, NF (Avicel PH-101) | 1.00 kg |
| 5.0 | Lactose, NF (Hydrous, 310) | 2.00 kg |
| 5.0 | Ascorbic Acid, USP | 2.00 kg |
| 0.1 | Sodium Lauryl Sulfate, NF | 0.04 kg |
| 2.5 | Polyoxamer 237, NF | 1.00 kg |
| 0.5 | Polyoxamer 188, NF | 1.00 kg |
| 1.5 | Talc, USP | 0.60 kg |
| 0.5 | Polyethylene Glycol 400, NF | 0.20 kg |
| * | Purified Water, USP | 12.00 kg |
| 100.00 | | 40.00 kg |

*Purified Water, USP is removed during processing.

EXAMPLE 35

| % W/W | INGREDIENT | AMOUNT |
|---|---|---|
| 80.00 | Carbamazepine, USP | 32.00 kg |
| 2.5 | Microcrystalline Cellulose, NF (Avicel PH-101) | 1.00 kg |
| 5.0 | Lactose, NF (Hydrous, 310) | 2.00 kg |
| 5.0 | Citric Acid, USP | 2.00 kg |
| 0.5 | Sodium Lauryl Sulfate, NF | 0.20 kg |
| 5.0 | Polyethylene Oxide, NF | 2.00 kg |
| 1.5 | Talc, USP | 0.60 kg |
| 0.5 | Glycerin, USP | 0.20 kg |
| * | Purified Water, USP | 12.00 kg |
| 100.00 | | 40.00 kg |

*Purified Water, USP is removed during processing.

In addition, it is to be understood, however, that the scope of the present invention is not to be limited to the specific embodiments described herein and that the invention may be practiced other than as particularly described and still be within the scope of the accompanying claims.

What is claimed is:

1. A pharmaceutical composition comprising a robust pellet containing carbamazepine, said pellet containing carbamazepine in an amount of at least seventy weight percent and including a binder containing a high number average molecular weight polyvinylpyrrolidone in an amount of about 5 wt. %.

2. A pharmaceutical composition comprising:

a sustained release robust pellet containing carbamazepine, said pellet containing carbamazepine in an amount of at least seventy weight percent and including a binder containing a high number average molecular weight polyvinylpvrrolidone in an amount of about 5 wt. %.

3. A pharmaceutical composition comprising:

an enteric release robust pellet containing carbamazepine, said pellet containing carbamazepine in an amount of at least seventy weight percent and including a binder containing a number average molecular weight polyvinylpyrrolidone in an amount of about 5 wt. %.

4. The composition of claim 1 wherein said polyvinylpyrrolidone has a number average molecular weight of at least 100,000.

5. The composition of claim 2 wherein said polyvinylpyrrolidone has a number average molecular weight of at least 100,000.

6. The composition of claim 2 and further comprising a coating material, wherein said coating material is present in an amount of from about 1.0% (w/w) to about 25% (w/w).

7. The composition of claim 6 wherein said coating material is present in an amount of from about 10% (w/w) to about 20% (w/w).

8. The composition of claim 2 wherein said polyvinylpyrrolidone has a number average molecular weight of at least 100,000.

9. The composition of claim 3 and further comprising a coating material, wherein said coating material is present in an amount of from about 1.0% (w/w) to about 25% (w/w).

10. The composition of claim 9 wherein said coating material is present in an amount of from about 10% (w/w) to about 20% (w/w).

* * * * *

UNITED STATES PATENT AND TRADEMARK OFFICE
CERTIFICATE OF CORRECTION

PATENT NO.   : 5,912,013
DATED        : June 15, 1999
INVENTOR(S)  : Edward M. Rudnic et al.

Page 1 of 1

It is certified that error appears in the above-identified patent and that said Letters Patent is hereby corrected as shown below:

<u>Title page,</u>
Item [75], Inventor(s), delete "; John McCarty, Biscayne Park, Fla.; Sandra Wassink, Frederick; Richard A. Couch, Germantown, both of Md.".

Signed and Sealed this

Eighteenth Day of March, 2003

JAMES E. ROGAN
*Director of the United States Patent and Trademark Office*